United States Patent [19]

Pfirrmann

[11] Patent Number: 6,080,397
[45] Date of Patent: Jun. 27, 2000

[54] COMPOSITIONS COMPRISING PVP HAVING AN AVERAGE MOLECULAR WEIGHT IN THE RANGE OF 3.000 TO 14.000 DALTONS

[75] Inventor: Rolf Wilhelm Pfirrmann, Lucerne, Switzerland

[73] Assignee: Ed. Geistlich Sohne AG fur Chemische Industrie, Switzerland

[21] Appl. No.: 09/091,228

[22] PCT Filed: Jan. 9, 1997

[86] PCT No.: PCT/GB97/00069

§ 371 Date: Sep. 4, 1998

§ 102(e) Date: Sep. 4, 1998

[87] PCT Pub. No.: WO97/25052

PCT Pub. Date: Jul. 17, 1997

[30] Foreign Application Priority Data

Jan. 10, 1996 [GB] United Kingdom .................. 9600426

[51] Int. Cl.[7] .............................. A61K 9/08; A61K 31/79
[52] U.S. Cl. ........................ 424/78.08; 422/28; 514/833; 210/692
[58] Field of Search ............................... 424/78.32, 78.08

[56] References Cited

U.S. PATENT DOCUMENTS 4,350,156  9/1982  Malchesky et al. ................. 128/214 R

FOREIGN PATENT DOCUMENTS

| 0139535 | 5/1985 | European Pat. Off. . |
|---|---|---|
| 0147021 | 7/1985 | European Pat. Off. . |
| 3536560 | 4/1986 | Germany . |
| 2165752 | 4/1986 | United Kingdom . |

OTHER PUBLICATIONS

C.A. 94:71523 R.W. Pfirrmann et al DE 3017711 Nov. 1980.

C.A. 124:97697 D. Jones et al 1995 C.A. 94:202400.

Janik et al., "Prevention of Postoperative Peritoneal Adhesions, Efficacy of Povidone", Archives of Surgery, vol. 117, No. 10, pp. 1321–1324, 1982.

Dr. Herbert P. Fiedler, "Lexikon Der Hilfsstoffe Für Pharmazie, Kosmetik Und Angrenzende Gebiette", Editor Cantor, pp. 695.

*Primary Examiner*—Peter F. Kulkosky
*Attorney, Agent, or Firm*—Rothwell, Figg, Ernst & Kurz, p.c.

[57] ABSTRACT

The present invention relates to compositions for use in medicine, e.g. as infusion or surgical rinse solutions, and to processes for their preparation. The compositions of the invention comprise an aqueous solution of physiologically inert PVP having a weight average molecular weight in the range of from 3,000 to 14,000 daltons.

15 Claims, No Drawings

COMPOSITIONS COMPRISING PVP HAVING AN AVERAGE MOLECULAR WEIGHT IN THE RANGE OF 3.000 TO 14.000 DALTONS

The present invention relates to polyvinylpyrrolidone (PVP) compositions for use in medicine, in particular as injection, infusion and surgical rinse solutions and as plasma expanders.

Infusion solutions, which are administered in relatively large volumes, commonly contain PVP to provide a colloid osmotic pressure similar to that of blood and to assist in stabilising relatively insoluble components in such solutions. In particular, infusion solutions containing the antibacterial compound taurolidine have been formulated with PVP to maintain a relatively high taurolidine concentration. Similarly, taurolidine solutions for injection have also been formulated with PVP.

Surgical rinse solutions are used either during or immediately after surgery to irrigate body tissues and generally contain a synthetic colloidal material to bind water and thus reduce the incidence of oedema.

Plasma expanders are used to replace or maintain blood volume. Except in the case of major blood loss when replacement of blood constituents is necessary, whole blood is not used for simple expansion of blood volume due to difficulties with availability and cross matching. A number of synthetic plasma substitutes, e.g. colloidal solutions of dextrans, gelatin and starch derivatives, are currently in use. Synthetic plasma substitutes have the additional advantages of lower viscosity which enables early improvement in microcirculation and erythrocyte aggregation. Synthetic plasma substitutes are particularly useful in the rheological therapy of peripheral and cerebral circulatory disturbances due to improved oxygen supply to the ischaemic tissue, and in the treatment of sepsis.

However, the colloidal materials currently in use are associated with hypersensitivity reactions, which limits their use. For example, infusions of dextrans, gelatin or hydroxy ethyl starch (HES) may produce hypersensitivity reactions such as itching, fever, joint pains and hypotension, as well as severe cases of anaphylactic reactions. HES is potentially nephrotoxic and can lead to acute kidney failure and the storage of HES in various body tissues can also lead to severe long term itching. In part, such effects are may be due to metabolic degradation of such colloids as well as any impurities present.

Polyvinylpyrrolidone (PVP), also commonly known as povidone or polyvidone, is a synthetic polymer consisting essentially of linear chains comprising repeating N-vinyl-2-pyrrolidone units, the degree of polymerisation resulting in polymers of various molecular weights according to a Gaussian distribution. Indicative of its molecular weight is its viscosity in aqueous solution, relative to that of water. This is expressed as a K-value which may range from 10 to 120.

An important property of PVP is its universal solubility which extends from hydrophilic solvents such as water to hydrophobic solvents such as butanol. This makes PVP particularly well suited to use as a blood replacement solution. However, the consequences of exposure of the human body to PVP solutions have been the subject of much study.

Although PVP solutions are, in general, well tolerated, it is now well established that high molecular weight PVP when administered in large amounts intravenously can be partly stored in the body. The extent of PVP uptake into tissues is dependent upon a number of factors, such as the molecular weight of the material and the amount of PVP administered, as well as the site and frequency of administration.

The various adverse effects associated with long term storage of PVP have been found to be related to the PVP fractions with relatively high molecular weight. It has been demonstrated that PVP molecules having a molecular weight up to about 30,000 daltons are excreted rapidly by glomerular filtration. Above this limit, e.g. up to about 70,000 daltons, excretion via the kidney is still possible but this is slower. Long term storage of high molecular weight PVP seems to be solely or mainly associated with uptake in the reticuloendothelial system (RES).

When administered over prolonged periods of time very high doses of PVP, particularly that containing high molecular weight fractions, can cause what is known as "PVP-storage disease" (Dupont-Lachapelle disease) which is characterised by symptoms such as dermatosis, rheumatic joint complaints and pulmonary changes with increasing respiratory insufficiency. Furthermore, a foamy appearance has been noted in the endothelial cells, tubular epithelia and glomerular epithelia of the kidney, in the Kupfer cells of the liver and in macrophages in the adrenal cortex. The extent of these changes is dependent upon the molecular weight (greatest storage with highest molecular weight). The aggregation of the storage cells to form liver granulomas may be dependent on T-lymphocyte function. Evidence from a number of in vivo and in vitro studies in the rat shows that PVP enters cells mainly by fluid-phase pinocytosis. PVP may also enter cells by phagocytosis where this process has been stimulated by the presence of other substances.

As a result, high molecular weight PVP has not been used parenterally for a number of years and has been largely replaced by albumin, dextran, hydroxy ethyl starch (HES) and gelatin preparations.

Low molecular weight PVP having a weight average molecular weight of 9,000 and a K-value of less than 17 has been found to be a non-allergenic colloid which is quickly absorbed from the blood stream and excreted unchanged via the kidneys. Commercially available low molecular weight PVP however still contains an unacceptably high proportion of PVP molecules having a molecular weight in excess of 50,000 daltons, e.g. up to 3% by weight.

Moreover, commercially available low molecular weight PVP has been found to contain a large number of impurities in trace amounts formed as a result of the free radical polymerisation processes used for its preparation. Such processes may be carried out in water or in organic solvents. Depending on the particular process used, such impurities may include unchanged monomer, solvent residues, hydrazine, acetaldehyde, formic acid and, in particular, triethylamine and peroxides. Such impurities may directly cause side effects, e.g. hydrazine is carcinogenic; formic acid is toxic and can cause a metabolite acidosis. Acetaldehyde gives an interaction with the applied pharmaceutica; the monomer and its derivatives, together with amino acids, e.g. serine or taurolidine, causes a reddish colour to the solution following sterilisation with steam and this is unacceptable in a pharmaceutical. Peroxides oxidise the solution creating an unacceptable yellowish colour in the infusion/instillation solution.

To date, the presence of high molecular weight PVP molecules and impurities has restricted the use of low molecular weight PVP solutions.

There thus exists the need for a high purity, non-allergenic, cell compatible colloid suitable for use as a colloid volume substitute, in particular as an infusion or surgical rinse solution.

Viewed from one aspect the present invention provides a composition suitable for use in medicine, in particular as an infusion or surgical rinse solution, comprising an aqueous solution of physiologically inert PVP having a weight average molecular weight in the range of from 3,000 to 14,000 daltons, preferably having a K-value of less than 17, e.g. between 15 and 16.

Preferably, the compositions of the invention are substantially free from PVP having a molecular weight above 50,000 daltons, e.g. they contain less than 1% by weight of PVP having a molecular weight in this range.

As used herein the term "physiologically inert" means that the PVP material does not exert any undesired physiological effects and this requires, primarily, that it is substantially free from contaminants such as triethylamine or acetaldehyde, or solvents such as isopropanol, t-butanol or acetone. In particular, the amount of amine present in the PVP material is preferably less than 10 parts per million (ppm). The amount of peroxide present is preferably less than 20 ppm and the amounts of solvent and monomer present are conveniently less than 10ppm and less than 2 ppm respectively. Conveniently, the PVP material is substantially free from any chemical impurities.

The low molecular weight PVP compositions in accordance with the invention are eliminated relatively rapidly from the kidneys with no biotransformation and thus present no long term adverse problems due to metabolic degradation. Furthermore, these may be used without risk of anaphylactic or itching reactions and in addition present no side effects due to the presence of impurities.

Low molecular weight, ultra-pure PVP compositions in accordance with the invention are rapidly excreted renally, or by dialysis, and therefore provide an excellent and well-tolerated colloid for intravenous infusions.

In general, it is preferred that the weight average molecular weight of the PVP is in the range of from 7,000 to 12,000 daltons, e.g. from 7,000 to 11,000 daltons. PVP having a weight average molecular weight of about 10,000 daltons is particularly preferred. At a concentration of 5% by weight in water this gives a colloid osmotic pressure of about 20 mOsm/litre.

In general the concentration of the PVP will be in the range of from 4 to 10% by weight, e.g. 5 to 6% by weight. An ultra-pure 5% PVP solution in $CO_2$-free distilled water can be expected to have a pH value between 6.5 and 7.2. This is to be compared to such a solution containing traces of triethylamine which may cause the pH to rise to 9.8.

Conventional infusion or surgical rinse solutions preferably contain an antibacterial to combat infections. The antibacterial compounds taurultam and taurolidine have been found to be particularly effective in combating not only infecting bacteria but also the resultant toxins. Furthermore, they are capable of exerting an antioxidant effect against oxygen free radicals. Taurultam and taurolidine are also formulated for infusion and injection in combating endo- and exotoxaemia in solutions containing low molecular weight PVP as stabiliser and colloid.

A preferred form of the compositions of the invention thus contains an effective concentration of taurolidine and/or taurultam, e.g. a bacterially effective concentration or an anti-toxin/anti-bacterial concentration. Such compositions may be used in the form of a solution in the treatment of infection or sepsis or as an anti-mediator therapy to reduce high macrophage-cytokine synthesis of TNF, IL-1 and IL-6. The concentration of taurolidine is advantageously in the range of from 0.5 to 2.0% by weight; the concentration of taurultam is advantageously in the range of from 1 to 10% by weight.

A particular advantage associated with the use of taurolidine and/or taurultam as an antibacterial is that these can withstand sterilisation by autoclaving whereas many conventional antibacterials such as penicillin can not.

In general, the compositions of the invention when formulated with taurolidine and/or taurultam will be approximately isotonic and will have an osmolality greater than 250 mOsm/litre, e.g. in the range 270–300 mOsm/litre, for example about 280–290 mOsm/litre. This osmolality will be predominantly due to electrolytes. Examples of suitable cations and anions include sodium, potassium, calcium, chloride, lactate, maleate and bicarbonate. It is possible, however, to administer via a central catheter without electrolytes, in which case the osmotic pressure would be lower, e.g. 145 mOsm/litre.

Conventionally, PVP is produced by free radical polymerisation of N-vinylpyrrolidone either in water using hydrogen peroxide as an initiator or in an organic solvent, e.g. isopropanol. The latter process is used today for the production of low molecular weight PVP for injection solutions. Termination of the polymerisation reaction enables the preparation of PVP of almost any molecular weight.

Both methods yield polymers in solution form. In the isopropanol method the alcohol is removed by distillation and subsequently converted to an aqueous solution by steam distillation. Distillation using pure steam removes most of the impurities. If desired, the low and medium molecular weight polymers are spray dried to produce the pharmaceutical grade PVP powders, while the high molecular weight grades are roller dried.

Conventionally, PVP solutions are purified by steam distillation to remove any triethylamine. Whilst this removes most of the amine, residual amine raises the pH to over 9.0 and lactic acid is commonly added to reduce the pH. However, the amine is still present and tends to form nitrosamines which can be toxic, particularly as a result of infusion over a period of several months. As a result of the presence of impurities such as monomeric vinylpyrrolidone, and amino acids such as serine or taurine, the resulting PVP solutions turn red in colour when formulated with taurolidine or taurultam. In the context of an infusion or surgical rinse solution this is unacceptable.

Any unreacted peroxides present in the PVP solutions tend to turn this yellow in colour following sterilisation. In the context of an infusion or surgical rinse solution this colouring too is undesirable. To remove this colouring, bisulphite is conventionally added, which is undesirable in an infusion solution.

We have now found that a low molecular weight PVP solution of high purity can be prepared through the use of ion exchange chromatography which not only removes the excess amine but also ensures removal of any traces of peroxide.

Thus, viewed from a further aspect the invention provides a process for the preparation of a high purity, low molecular weight PVP solution, said process comprising the step of passing a PVP solution over a cation exchange resin. To ensure removal of any high molecular weight PVP molecules, this is preferably followed by ultrafiltration.

The high purity PVP solutions prepared in accordance with the process of the invention have the advantage that these remain colourless following sterilisation and formulation with taurolidine or taurultam. Moreover, as a result of removal of any traces of peroxide, there is no need to add bisulphite to the solutions following sterilisation.

Chromatography is conveniently carried out using a cation exchange resin, e.g. an acid cation exchange resin.

Whilst either strong or weak acid cation exchangers may be used, strong acid cation exchangers are preferred. Examples of suitable weak acid cation exchangers are those in which the active group is a carboxylic acid, e.g. Dowex® CCR-2 and Dowex® MWC-1 (available from Dow Corning, USA). Preferred as strong acid cation exchangers are those in which the active group is a sulphonic acid, e.g. Dowex® MSC-1.

Elimination of any PVP molecules having a molecular weight between 50,000 and 100,000 daltons is conveniently carried out by ultrafiltration. In this way, the high molecular weight PVP which is known to cause the unwanted storage problems can be reduced to less than 3% by weight, e.g. to about 1% by weight. If desired, ultrafiltration can be carried out at a transmembrane pressure of from 100 to 500 mm Hg.

Ultrafiltration is conveniently carried out using a hydrophilic polyamide membrane, e.g. using Ultrafilter U 7000 available from Gambro AB, Sweden.

The PVP solutions are then conveniently sterilised prior to use. In general this is carried out by autoclaving at a temperature of from 115 to 125° C., e.g. from 120 to 121° C. for 10 to 20 mins, e.g. 15 to 16 mins.

If desired, the resulting PVP solution can be converted into powder form by spray drying the solution under a protective nitrogen atmosphere. This ensures that no undesirable peroxides are formed. Auto-oxidation can increase the peroxide content of PVP on storage. Highly purified PVP powders should therefore preferably be hermetically sealed in air-tight combibags (polyethylene/aluminium foil).

The compositions according to the invention are of particular use as infusion, electrolyte and haemodilution solutions as well as surgical rinse solutions. In particular, the compositions may be used as short-term plasma expanders and blood substitutes, for increasing the oncotic pressure in infusion solutions without any antigenic effect, and in the treatment of blood loss, sepsis and burns. Such use provides volume stability; in contrast to pure electrolyte solutions which rapidly traverse the tissue of the intravasal area, the PVP solutions exert a volume effect due to the ability of PVP to bind water. In general, microcirculation, haematocrit reading, erythrocyte deformation, erythrocyte aggregation and blood and plasma viscosity are improved (e.g. in peripheral and arterial obstruction diseases) and hypervolemic haemodilution lowers the plasma viscosity and increases blood circulation. The oxygen supply may also be improved. Elimination of impurities and high molecular weight PVP avoids any side effects due to these factors and enables the PVP to be administered safely at high dosage levels. The PVP solutions of the invention may thus be beneficial in treatment of coronary heart disease, disturbances of cerebral blood flow, idiopathic hearing disturbances (by improvement of the blood flow to the inner ear) and chronic arterial blockage diseases; in improving the prognosis in patients suffering from stroke or apoplexy; in the therapy and prophylaxis of blood volume depletion, for example in haemorrhagic, traumatic or septic shock, in surgical operations and in the treatment of burns; and for therapeutic blood thinning (haemodilution).

Thus, viewed from a further aspect the invention provides a composition in accordance with the invention for use in medicine, in particular as an infusion or surgical rinse solution.

Viewed from a further aspect the invention provides the use of PVP as defined above in relation to the compositions of the invention in the manufacture of an infusion or surgical rinse solution.

Viewed from a further aspect the invention provides a method of infusion or surgical rinsing of tissues of the human or non-human animal body whereby the tissues are perfused with a composition in accordance with the invention.

The dose and rate of infusion of the compositions of the invention depends on the PVP content and on the clinical situation; for example the dosage for a 2% taurolidine solution containing 5% PVP is 250 ml/2 hrs drop infusion per 70 kg body weight via a central catheter.

For plasma expansion or fluid replacement (i.e. PVP plus electrolytes), 2 to 4 ml per kg body weight/hour would be introduced by drop infusion. Following severe surgery and blood loss, the amount can be increased to 6 ml per kg body weight per hour. The exact rate in ml per hour depends on several individual factors such as operation technique, length of the operation, pre-operative introduction of electrolytes and nutritional condition.

The invention will now be further illustrated by way of the following non-limiting examples:

EXAMPLE 1

(a) Purification of PVP 17 PF 100 g acid ion resin exchanger Dowex No. MSC-1 in sodium form are filled into a glass chromatographic column having an inner radius of 4 cm and a height of 50 cm, and then rinsed with fresh distilled pyrogen-free water.

Following this the resin is activated by acidifying with 200 ml 0.5 N HCl. Rinsing then takes place with fresh distilled water until the eluate is chloride free and a pH of approximately 4.5 to 5.3 exists.

A 10% PVP 17 PF solution (BASF, Germany) which contains traces of triethylamine with a pH of approximately 9.35 is then added to the column at a drop speed of 1000 ml per hour. The eluate is then collected and evaporated in a vacuum vaporizer. This produces an amorphous, nearly colourless, amine-free, brittle PVP powder which can be used in infusion and instillation solutions, as well as for surgical rinse solutions. Although the PVP may be used following this stage of purification, it is preferable to also remove high molecular weight PVP from the product (see step (b) below).

On a larger scale the solution is purified through a technical stainless steel ion resin exchanger and spray dried under nitrogen gas to prevent formation of peroxides and auto-oxidation.

(b) Removal of High Molecular Weight PVP 2 kg of the product from (a) above and 18 kg of distilled pyrogen-free water for injection is introduced into a stainless steel container attached via a plastic tube to a Gambro 7000 Ultrafilter. A pressure of 0.7 atmospheres is then applied. About 70 to 90 ml ultrafiltrate is extracted per minute. The PVP content of the ultrafiltrate is about 8% by weight.

The amount of PVP having a molecular weight over 30,000 daltons (determined by gel permeation chromatography) is reduced from about 9.8 to 11.0% by weight to about 1.7 to 2.0% by weight. The average molecular weight is in the range of 7000 to 9000 daltons.

The resulting product is highly purified and is referred to hereinafter as PVP 17 PF UP.

EXAMPLE 2

Slow Intravenous Drop Infusion

| | | | |
|---|---|---|---|
| (a) | PVP 17 PF UP | | 30 g |
| | Sodium chloride | | 4.5 g |
| | Water for injection | ad | 500 ml |

|     |                    |    |        |
| --- | ------------------ | -- | ------ |
|     | pH 7.3             |    |        |
| (b) | PVP 17 PF UP       |    | 50 g   |
|     | Sodium chloride    |    | 4.0 g  |
|     | Water for injection | ad | 500 ml |
|     | pH 7.3–7.4         |    |        |

The above solutions are hyperoncotic and may be used for the short-term stabilisation of the blood circulation both pre- and post-operatively. Infusion of 500 ml of such solutions increases blood volume for 3 to 4 hours.

EXAMPLE 3
Surgical Rinse Solutions with Bactericide

|     |                                                                                                                                        |    |         |
| --- | -------------------------------------------------------------------------------------------------------------------------------------- | -- | ------- |
| (a) | PVP 17 PF UP                                                                                                                           |    | 50.0 g  |
|     | Sodium⁺                                                                                                                                |    | 3.382 g |
|     | Potassium⁺                                                                                                                             |    | 0.157 g |
|     | Calcium⁺⁺                                                                                                                              |    | 0.090 g |
|     | Chloride⁻                                                                                                                              |    | 5.520 g |
|     | Chlorhexidine hydrochloride*                                                                                                           |    | 0.5 g   |
|     | Sterile water                                                                                                                          | ad | 1 liter |
| (b) | Formulation (a) with chlorhexidine replaced by 5.0 g taurolidine, or 10.0 g taurultam.                                                 |    |         |
| (c) | Formulation (a) with chlorhexidine replaced by 10.0 g neomycin sulphate/bacitracin (0.1 g dry substance contains 32,500 I.U. neomycin sulphate and 2,500 I.U. bacitracin). |    |         |

*The chlorhexidine hydrochloride has a tendency to slowly crystallise in solution. However, the PVP also acts as a crystallisation inhibitor.
In (a) and (b) the resulting solutions are sterile filtered.

EXAMPLE 4
Surgical Rinse Solution for Local Rinsing

|     |                          |    |          |
| --- | ------------------------ | -- | -------- |
| (a) | PVP 17 PF UP             |    | 12.50 g  |
|     | Sodium chloride          |    | 6.00 g   |
|     | Calcium chloride.6H₂O    |    | 0.15 g   |
|     | Potassium chloride       |    | 0.075 g  |
|     | Sodium hydrogen carbonate|    | 0.075 g  |
|     | Taurolidine              |    | 5.00 g   |
|     | Sterile water            | ad | 1 liter  |
| (b) | PVP 17 PF UP             |    | 12.50 g  |
|     | Sodium chloride          |    | 6.00 g   |
|     | Calcium chloride.2H₂O    |    | 0.27 g   |
|     | Potassium chloride       |    | 0.4 g    |
|     | Sodium lactate 50% solution |  | 6.1 g    |
|     | Taurolidine              |    | 5.00 g   |
|     | Sterile water            | ad | 1 liter  |

EXAMPLE 5
Infusion Solution

|     |                          |    |          |
| --- | ------------------------ | -- | -------- |
| (a) | PVP 17 PF UP             |    | 60.00 g  |
|     | Sodium chloride          |    | 6.90 g   |
|     | Potassium chloride       |    | 0.30 g   |
|     | Sodium lactate 50% Solution |  | 4.48 g   |
|     | Water for injection      | ad | 1 liter  |
| (b) | PVP 17 PF UP             |    | 60.00 g  |
|     | Sodium chloride          |    | 6.90 g   |
|     | Potassium chloride       |    | 0.30 g   |
|     | Calcium chloride dihydrate |  | 0.22 g   |
|     | Sodium lactate 50% solution | | 4.48 g   |
|     | Water for injection      | ad | 1 liter  |

| | |
|---|---|
| (c) | As (b) above with 100.00 g PVP 17 PF UP per liter. |
| (d) | As (b) above with 50.00 g PVP 17 PF UP per liter. |

The above solutions are adjusted to pH about 7.7 with a few drops of 0.1 N sodium hydroxide and all traces of oxygen are removed by evacuation and introduction of nitrogen. Subsequently, the solutions are sterile filtered using a 0.45µ PAL-prefiltered and a 0.22µ PAL sterile filter and filled into infusion flasks under nitrogen. Sterilisation is effected at 121° C. for 16 minutes in a stream of steam. The solutions are approximately isotonic or weakly hyperoncotic. The pH after sterilisation is about 6–7.

EXAMPLE 6
Infusion Solution for Therapy of Hypovolemia: Volume Substitution

|                          |    |         |
| ------------------------ | -- | ------- |
| PVP 17 PF UP             |    | 60.0 g  |
| Sodium chloride          |    | 6.4 g   |
| Potassium chloride       |    | 0.37 g  |
| Magnesium chloride.6H₂O  |    | 0.51 g  |
| Sodium acetate.3H₂O      |    | 3.4 g   |
| L-Malic acid             |    | 0.6 g   |
| Sterile water            | ad | 1 liter | pH with 0.1 N Sodium hydroxide approx. 7.7.
After sterilisation pH approx. 6–7.

EXAMPLE 7
Sodium Chloride-Free Infusion Solution for Therapy of Hypovolemia and Shock

|                            |    |         |
| -------------------------- | -- | ------- |
| PVP 17 PF UP               |    | 60.0 g  |
| D-Glucose Monohydrate      |    | 55.0 g  |
| (Dextrose, USP 23)         |    |         |
| Sterile water              | ad | 1 liter |
| pH 4–6                     |    |         |

EXAMPLE 8
Drop-Infusion Solution for Bacteraemia and Sepsis

|                |    |        |
| -------------- | -- | ------ |
| PVP 17 PF UP   |    | 5.0 g  |
| Taurolidine    |    | 2.0 g  |
| Sterile water  | ad | 100 ml | pH after sterilisation 7.2–7.3
hyperton. ca. 145 mOsm/l
Bottles of 100 ml, 250 ml and 500 ml

EXAMPLE 9
Drop-Infusion Solution for Bacteraemia and Septic Shock

|                       |    |        |
| --------------------- | -- | ------ |
| PVP 17 PF UP          |    | 25.0 g |
| Taurolidine           |    | 10.0 g |
| D-Glucose monohydrate |    | 50.0 g |
| Sterile water         | ad | 500 ml | pH after sterilisation 6.4–6.8
hyperton. ca. 630 mOsm/l
Bottles of 500 ml

What is claimed is:
1. A composition suitable for use in medicine as an infusion solution, a haemodilation solution or a surgical rinse solution, comprising an aqueous colloidal solution of physiologically inert PVP having colloidal osmotic pressure and a weight average molecular weight in the range of from 7,000 to 12,000 Daltons, said solution being substantially free of chemical impurities with an amine content of less than about 10 ppm, a peroxide content of less than about 20 ppm, a solvent content of less than about 10 ppm wherein said solvent is isopropanol, t-butanol or acetone, and being substantially free from PVP having a molecular weight above 50,000 Daltons.

2. The composition of claim 1 having a monomer content of less than about 2 ppm.

3. The composition of claim 1 wherein said weight average molecular weight is in the range of from 7,000 to 11,000 Daltons.

4. The composition of claim 1 wherein said weight average molecular weight is in the range of from 10,000 to 11,000 Daltons.

5. The composition of claim 1 having a K-value of less than 17.

6. The composition of claim 5 having a K-value in the range of from 15 to 16.

7. The composition of claim 1 wherein the concentration of PVP is in the range of from 4 to 10% by weight.

8. The composition of claim 1 further comprising an effective concentration of taurolidine, tarultam or a combination thereof.

9. The composition of claim 8 comprising from 0.5 to 2% by weight taurolidine, from 1 to 10% by weight tarultam or a combination thereof.

10. A process for the preparation of a composition suitable for use in medicine as an infusion solution, a haemodilation solution or a surgical rinse solution, comprising an aqueous colloidal solution of physiologically inert PVP having colloidal osmotic pressure and a weight average molecular weight in the range of from 7,000 to 12,000 Daltons, said solution being substantially free of chemical impurities with an amine content of less than about 10 ppm, a solvent content of less than about 10 ppm wherein said solvent is isopropanol, t-butanol or acetone, a peroxide content of less than about 20 ppm, and being substantially free from PVP having a molecular weight above 50,000 Daltons, said process comprising a step of passing a PVP solution over a cation exchange resin.

11. The process of claim 10 further comprising ultrafiltration of said PVP solution after passing said PVP solution over said cation exchange resin.

12. The process of claim 10 wherein said cation exchange resin is a strong acid cation exchanger.

13. The process of claim 11 wherein said ultrafiltration is carried out at a pressure of from 100 to 500 mm Hg.

14. A composition prepared according to the process of claim 10 said composition being suitable for use in medicine as an infusion solution, a haemodilation solution or a surgical rinse solution, said composition comprising an aqueous colloidal solution of physiologically inert PVP having colloidal osmotic pressure and a weight average molecular weight in the range of from 7,000 to 12,000 Daltons, said solution being substantially free of chemical impurities with an amine content of less than about 10 ppm, a solvent content of less than about 10 ppm wherein said solvent is isopropanol, t-butanol or acetone, a peroxide content of less than about 20 ppm, and being substantially free from PVP having a molecular weight above 50,000 Daltons.

15. The composition of claim 1 having a monomer content of less than about 2 ppm.

* * * * *